United States Patent
Saeki

(10) Patent No.: US 9,173,599 B2
(45) Date of Patent: Nov. 3, 2015

(54) LANCET

(71) Applicant: ASAHI POLYSLIDER COMPANY, LIMITED, Osaka (JP)

(72) Inventor: Hideaki Saeki, Okayama (JP)

(73) Assignee: ASAHI POLYSLIDER COMPANY, LIMITED, Osaka (JP)

( * ) Notice: Subject to any disclaimer, the term of this patent is extended or adjusted under 35 U.S.C. 154(b) by 0 days.

(21) Appl. No.: 14/124,438

(22) PCT Filed: Jan. 10, 2013

(86) PCT No.: PCT/JP2013/050867
§ 371 (c)(1),
(2) Date: Dec. 6, 2013

(87) PCT Pub. No.: WO2013/118554
PCT Pub. Date: Aug. 15, 2013

(65) Prior Publication Data
US 2014/0088631 A1 Mar. 27, 2014

(30) Foreign Application Priority Data
Feb. 8, 2012 (JP) ................................. 2012-025246

(51) Int. Cl.
*A61B 17/32* (2006.01)
*A61B 5/15* (2006.01)
*A61B 5/151* (2006.01)

(52) U.S. Cl.
CPC ............. *A61B 5/1411* (2013.01); *A61B 5/1519* (2013.01); *A61B 5/150435* (2013.01);
(Continued)

(58) Field of Classification Search
CPC ........... A61B 5/15142; A61B 5/15144; A61B 5/15186; A61B 5/1411; A61B 5/150549; A61B 5/1519; A61B 5/150717; A61B 5/150022; A61B 5/15113; A61B 5/150435; A61B 5/150618; A61B 5/150519; A61B 5/15119; A61B 5/15117
USPC ........................... 606/181, 182, 183; 600/583
See application file for complete search history.

(56) References Cited

U.S. PATENT DOCUMENTS 3,358,689 A * 12/1967 Higgins ........................ 606/181
5,385,571 A 1/1995 Morita
(Continued)

FOREIGN PATENT DOCUMENTS

EP 1 767 149 3/2007
GB 2 352 403 1/2001
(Continued)

OTHER PUBLICATIONS

International Search Report (ISR) issued Feb. 19, 2013 in International (PCT) Application No. PCT/JP2013/050867.
(Continued)

*Primary Examiner* — Jing Ou
(74) *Attorney, Agent, or Firm* — Wenderoth, Lind & Ponack, L.L.P.

(57) ABSTRACT

There is provided a lancet comprising a lancet body, a lancet cap and a pricking component. In the lancet, the lancet body and the lancet cap are made of resin and the pricking component is made of metal. The pricking component is situated in both of the lancet body and the lancet cap, and the tip of the pricking component is covered with the lancet cap. The lancet body of the lancet is thin except for a rim portion of the body, and the rim portion of the lancet body has such a form that the rim portion extends symmetrically from the thinned portion of the lancet body.

4 Claims, 22 Drawing Sheets

(52) U.S. Cl.
CPC ..... *A61B5/150519* (2013.01); *A61B 5/150549* (2013.01); *A61B 5/150618* (2013.01); *A61B 5/150717* (2013.01); *A61B 5/150022* (2013.01); *A61B 5/15113* (2013.01); *A61B 5/15117* (2013.01); *A61B 5/15119* (2013.01); *A61B 5/15142* (2013.01)

(56) References Cited

U.S. PATENT DOCUMENTS

| | | | |
|---|---|---|---|
| 5,554,166 A | 9/1996 | Lange et al. | |
| 2003/0109895 A1* | 6/2003 | Taylor et al. | 606/181 |
| 2006/0129173 A1* | 6/2006 | Wilkinson | 606/181 |
| 2007/0162064 A1* | 7/2007 | Starnes | 606/181 |
| 2007/0225741 A1 | 9/2007 | Ikeda | |
| 2007/0293883 A1* | 12/2007 | Horie | 606/181 |
| 2009/0012551 A1* | 1/2009 | Nicholls | 606/181 |
| 2009/0069832 A1 | 3/2009 | Kitamura et al. | |
| 2009/0312781 A1 | 12/2009 | Hyoue | |
| 2010/0030249 A1* | 2/2010 | Pusey et al. | 606/181 |
| 2010/0160831 A1* | 6/2010 | Stout et al. | 600/583 |
| 2010/0305600 A1* | 12/2010 | Karbowniczek et al. | 606/182 |
| 2011/0009891 A1* | 1/2011 | Stout et al. | 606/181 |
| 2013/0012976 A1 | 1/2013 | Imori | |

FOREIGN PATENT DOCUMENTS

| | | |
|---|---|---|
| JP | 5-285127 | 11/1993 |
| JP | 7-16218 | 1/1995 |
| WO | 2007/018215 | 2/2007 |
| WO | 2007/097283 | 8/2007 |
| WO | 2009/006461 | 1/2009 |
| WO | 2011/043383 | 4/2011 |

OTHER PUBLICATIONS

Supplementary European Search Report (ESR) issued Aug. 26, 2014 in corresponding European Patent Application No. EP 13 74 6738.
English translation of the International Preliminary Report on Patentability issued Aug. 12, 2014 in International (PCT) Application No. PCT/JP2013/050867.

* cited by examiner

Before attaching of lancet to cylindrical attachment (Present Invention)

After attaching of lancet to cylindrical attachment (Present Invention)

After attaching of lancet to cylindrical attachment (Prior Art)

Fig. 9
Prior Art
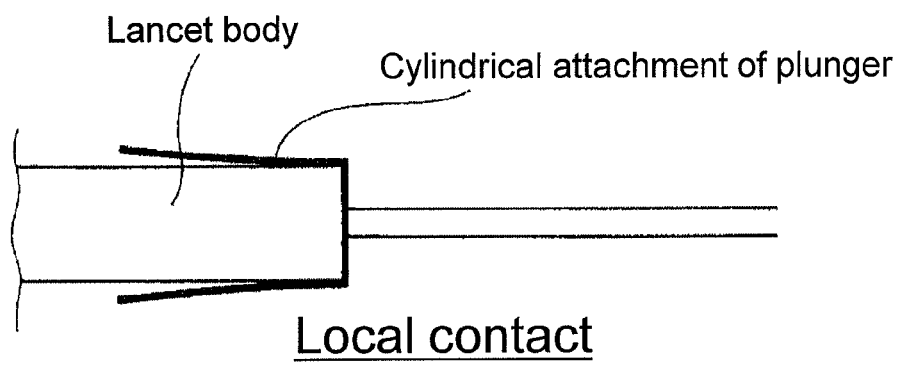
Local contact
Present Invention
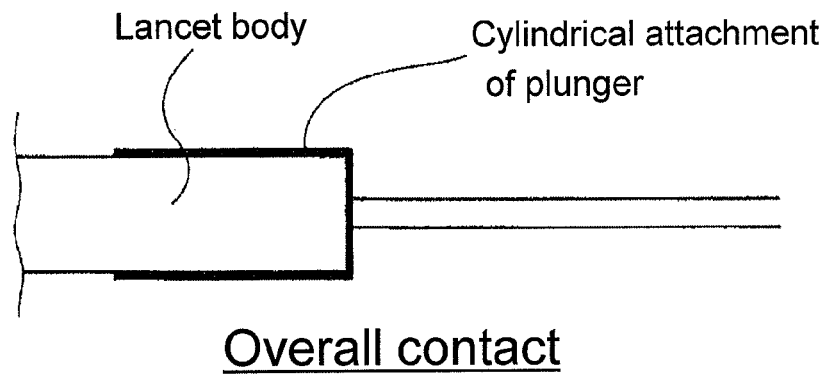
Overall contact Fig. 12
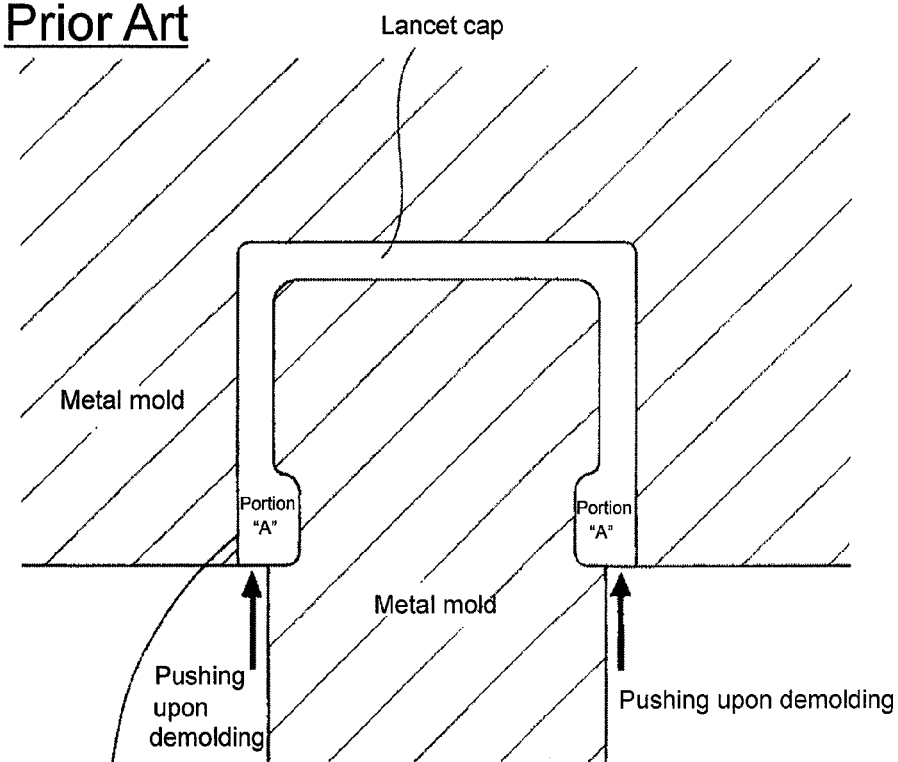
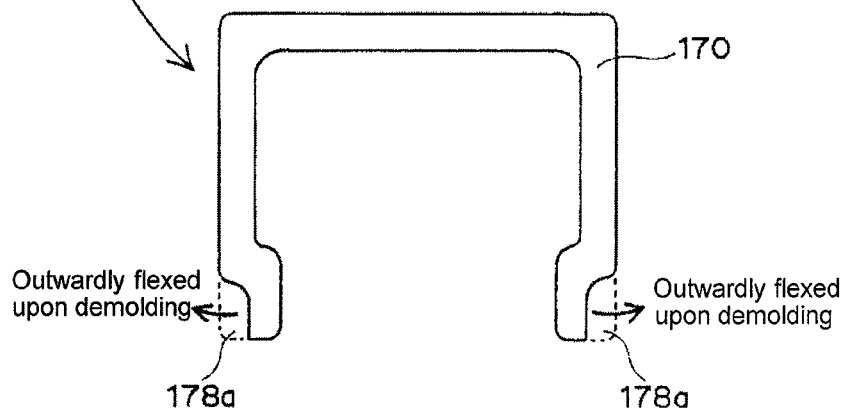

Fig. 13
| | Design | Weight percent ratio (with respect to LRV) | Material | Parts | Volume [cm³] | Specific weight [g/cm³] | Weight [g] | Total weight [g] |
|---|---|---|---|---|---|---|---|---|
| Lancet of Prior Art | 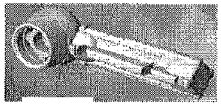 | 100% | PE-LD | Cap | 0.297 | 0.925 | 0.274 | 0.651 |
| | | | | Body | 0.407 | | 0.376 | |
| | | | PE-HD | Cap | 0.297 | 0.95 | 0.282 | 0.668 |
| | | | | Body | 0.407 | | 0.387 | |
| Lancet of Present Invention | 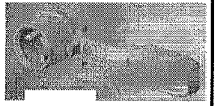 Cutout Cap | 60.0% | PE-LD | Cap | 0.185 | 0.925 | 0.171 | 0.390 |
| | | | | Body | 0.237 | | 0.219 | |
| | | | PE-HD | Cap | 0.185 | 0.95 | 0.176 | 0.401 |
| | | | | Body | 0.237 | | 0.225 | |
| | 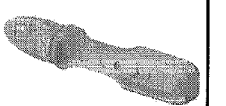 Flat head | 42.4% | PE-LD | Cap | 0.064 | 0.925 | 0.059 | 0.276 |
| | | | | Body | 0.234 | | 0.216 | |
| | | | PE-HD | Cap | 0.064 | 0.95 | 0.061 | 0.283 |
| | | | | Body | 0.234 | | 0.222 | |

LANCET

This application is the National Stage of International Application PCT/JP2013/050867, filed Jan. 10, 2013.

TECHNICAL FIELD

The present invention relates to a lancet. More specifically, the present invention relates to a lancet which is used for taking a sample of body fluid (e.g., blood).

BACKGROUND OF THE INVENTION

In order to measure a blood sugar level of a patient with diabetes, it is required to take a sample of the blood from the patient. The small amount of the blood to be taken can be enough. Thus, a lancet capable of taking a small amount of blood is used to measure the blood sugar level. The lancet is generally equipped with a pricking needle capable of puncturing a predetermined region of the patient's body (see, for example, U.S. Pat. No. 5,385,571).

In general, the lancet is used in conjunction with an injector. The injector has a function of launching the lancet toward the predetermined region. By loading the lancet into the injector, the pricking device is set up for use. The lancet loaded into the injector is launched toward the predetermined region by means of a plunger of the injector, whereby the predetermined region is pricked.

The present applicant has invented the following pricking device, and filed the application regarding such device (WO 2007/018215 A1, filed date: 8 Aug. 2006, title of the invention: "PRICKING DEVICE, AS WELL AS LANCET ASSEMBLY AND INJECTOR ASSEMBLY THAT CONSTITUTE THE PRICKING DEVICE"). Referring to the accompanying drawings, the lancet assembly and the injector assembly invented by the applicant will be briefly explained below (note that the term "lancet assembly" will be hereinafter referred to also as "lancet", and the term "injector assembly" will be hereinafter referred to also as "injector"). FIG. 14 shows an external appearance of a lancet 100', and FIG. 15 shows an external appearance of an injector 200'. As shown in FIGS. 16 and 17, the lancet 100' is composed of a lancet body 104', lancet cap 106' and a pricking component 105'. The pricking component 105' is attached to the lancet body 104', and the tip of the pricking needle is covered with the lancet cap 106'. The lancet cap 106' and the lancet body 104' are integrally connected together by a weakened part 108'. As shown in FIGS. 14 and 17, the protective cover 102' is provided to enclose a part of the lancet body 104'. Such lancet 100' is loaded into the injector 200', and thereafter the lancet cap 106' is removed. By the removal of the lancet cap, the tip of the pricking needle 105' is exposed, and thereby the lancet becomes ready for pricking.

The injector 200' shown in FIG. 15 can be used in combination with the lancet 100' to launch the lancet body with the tip of the pricking needle 105' exposed. The injector 200' comprises a plunger 204'. The plunger 204' is capable of engaging with a rear end portion of the lancet body to launch the lancet body in the pricking direction (see FIG. 18). As shown in FIG. 18, the lancet 100' is loaded into the injector 200' by inserting the lancet 100' into the injector 200' through a front end opening 214' of the injector 200'. As shown in FIG. 19, when the lancet is inserted to some degree, a rear portion 116' of the lancet 100' is held by tips 264' and 266' of the plunger 204'. Subsequently, when the insertion of the lancet is continued, the plunger 204' is thrust backward so that the launching energy is stored. That is, the retraction of the plunger 204' can compress a spring (not shown) provided in the plunger 204'. This means that, when the compression of the spring is released, the plunger instantly moves forward to launch the lancet. FIG. 20 shows the injector 200' in the state where the plunger has retracted and the launching energy has been stored therein.

After the loading of the lancet 100' into the injector 200' is completed, the lancet cap 106' is removed to expose the tip of the pricking needle 105'. The removal of the lancet cap 106' will be described as follows:

As shown in FIGS. 16 and 17, the lancet body 104' and the lancet cap 106' are integrally connected together by the weakened part 108' disposed between the lancet body and the lancet cap. The weakened part 108' is broken by rotating the lancet body 104' and the lancet cap 106' around the pricking needle in the reverse direction to each other (see FIG. 20 in which the rotation of the lancet cap in the direction "G" is shown), whereby the removal of the lancet cap 106' can be performed.

When the pricking operation is carried out, the front end opening 214' of the injector 200' is applied to a predetermined region to be pricked (for example, a finger tip). Subsequently, the press part 542' of a trigger component 514' is pushed. See FIG. 21. The pushing of the press part 542' results in an instantaneous expansion of the compressed spring, and thereby forcing the plunger 204' to move forwardly to prick the predetermined region with the pricking needle.

With respect to the injector, the tip of the plunge, to which tip the lancet is secured, mostly has a cylindrical portion (see FIG. 22). That is, the lancet is inserted into the cylindrical portion of the plunger, and thereby the lancet is secured to the plunger (see JP H05-285127). The lancet is more or less required to have an exact shape size with respect to the cylindrical portion. The exact shape size of the lancet makes it possible to firmly attach the lancet to the cylindrical portion of the plunger. In other words, if the cylindrical portion of the plunger does not have the exact shape size, the lancet cannot be attached to the plunger, and even if can be attached, the lancet is hard to be detached from the plunger at a point time after the pricking operation.

The lancet is used for the periodical measurement of the blood sugar level. This means that the lancet is used very often and disposable. Thus, it has been desired to keep the disposal amount of the used lancet as low as possible.

SUMMARY OF THE INVENTION

The present invention has been created in view of the above-mentioned circumstances. That is, one of objects of the present invention is to provide a lancet making it possible to not only achieve the attaching thereof to the injector without being largely affected by the shape size of the lancet-attachment portion of the plunger, but also contribute to the reduction of the disposal amount thereof after use.

In order to achieve the above object, the present invention provides a lancet comprising a lancet body, a lancet cap and a pricking component, wherein the lancet body and the lancet cap are made of resin and the pricking component is made of metal, the pricking component is situated in both of the lancet body and the lancet cap, the tip of the pricking component is covered with the lancet cap, wherein the lancet body is thin except for a rim portion thereof, and wherein the rim portion of the lancet body has such a form that the rim portion extends symmetrically from the thinned portion of the lancet body.

One feature of the present invention consists in the form of the lancet itself. Specifically, the lancet body is thin except for the rim portion of the lancet body. Another feature of the present invention consists in such a form that the rim portion of the lancet body extends symmetrically from the thinned portion of the lancet body.

The term "thin" as used herein means that the lancet body has a main portion which is thinner than the rim portion thereof. For example, the thinned main portion of the lancet body is thinner than the rim portion of the lancet body by 30% to 60%.

In a preferred embodiment of the lancet of the invention, the rim portion of the lancet body extends approximately perpendicularly with respect to the thinned portion (i.e., web portion) of the lancet body. More specifically, the rim of the lancet body approximately perpendicularly extends from each of edges of the thinned portion of the lancet body. As a result, the transverse section of the lancet body can have, for example, approximately "H-like" shape.

In another preferred embodiment, the rim portion of the lancet body is flexible such that the rim portion exhibits an inward flexibility. In other words, the lancet body can be inwardly flexed by an external force.

In use, the lancet is connected to "plunger provided in an injector for launching the pricking component". Upon the connection of the lancet to the plunger, the rim portion of the lancet body makes a surface contact with "cylindrical lancet attachment provided at the tip of the plunger". For example, the rim portion of the lancet body makes the surface contact with the cylindrical lancet attachment in a symmetrical form at four points of the rim portion.

In a preferred embodiment of the lancet of the invention, a rear part of the rim portion, which part is positioned at a rear side portion of the lancet body, extends symmetrically from the thinned portion of the lancet body. That is, the rim part of the lancet body, positioned on a plunger-connection side, has such a form that it extends symmetrically from the thinned portion of the lancet body.

It is preferred that an outer profile of the rim portion of the lancet body includes an arc shape in at least a part of thereof. In particular, the outer profile of the tip part of the rim ("tip part" in this case being called in view of the extending of the rim from the thinned portion) is preferably an arc shape or an "R" shape.

In another preferred embodiment, the lancet cap has a flat shape as a whole. It is preferred in this embodiment that the flat-shaped lancet cap has a thin portion which is thinner than a rim portion thereof.

It is preferred that a front end of the lancet body is provided with a flange portion "A". Similarly, a rear end of the lancet cap is preferably provided with a flange portion "B", and such flange portion "B" of the lancet cap is preferably opposed to the flange "A" of the lancet body.

In another preferred embodiment, the lancet cap has a cutout portion, and a periphery portion of the cap, which portion defines the cutout portion (especially defines an opening mouth of the cutout portion), has a stepped outer surface.

In still another preferred embodiment, the lancet body has a curved portion such that a width of the lancet body gradually decreases. It is preferred that a rear end of the lancet body has a sloped surface.

In accordance with the lancet of the invention wherein the lancet body is thin except for its rim portion, and also the rim portion of the lancet body extends symmetrically from a thin part of the body, the lancet can be attached to the injector without being largely affected by the size of the lancet-attachment portion of the plunger. Specifically, upon the attaching of the lancet to "cylindrical lancet attachment provided at the tip of the plunger", the rim portion of the lancet body can be inwardly flexed so that the lancet body corresponds to the size of the cylindrical lancet attachment of the plunger. That is, even if the size of the cylindrical lancet attachment is somewhat small, the lancet body can be flexed to suitably achieve the attaching of the lancet to the injector (i.e., the fitting of the lancet into the cylindrical lancet attachment). This means that the lancet can be attached to the plunger without relying on a flexing or the like of the cylindrical lancet attachment itself. As a result, the lancet of the present invention can be applied to various types of injectors, which provides a great versatility of the lancet.

In accordance with the lancet of the present, the flexed rim portion of the lancet body can make an entire contact with the cylindrical lancet attachment, which leads to an achievement of the relatively strong connection of the lancet to the plunger. In particular, the lancet body and the cylindrical lancet attachment (particularly, its inner wall surface) are not in "point contact", but in "surface contact" with each other, and thereby the lancet can be relatively strongly connected to the plunger, which allows a smooth removal of the lancet cap from the lancet. In a particularly preferred embodiment, they are in symmetrical "four" surface contact with each other at four points of the rim portion. Due to the surface contact of them, the reliable removal of the cap can be achieved by "twisting it off" (i.e., by "wrenching the lancet cap"), with the lancet attached to the injector prevented from being adversely rotated.

In accordance with the lancet of the invention, the lancet body is thin except for its rim portion, which largely reduces the weight and volume of the lancet. This can reduce not only the amount of the disposal amount of the lancet after use, but also the manufacturing cost by the decreased amount of the raw material of the lancet. The reduction in weight and volume of the lancet is achieved directly or indirectly by "flat-shaped lancet cap", "flange portion "A" of the lancet body/ flange portion "B" of the lancet cap", "cutout portion of the lancet cap", "curved portion of the lancet body", and "sloped surface of the rear end of the lancet body", in addition to the "thinned portion of the lancet body". As a result, the lancet of the present invention can reduce its weight and volume by 40% or more, and preferably by 50% or more (for example, about 50% to 65%) as compared to the conventional lancet (e.g., the prior art lancet 100' shown in FIG. 13 or 22). It should be noted that "thinned portion of the lancet body", "flat-shaped lancet cap", "flange portion "A" of the lancet body/flange portion "B" of the lancet cap", "cutout portion of the lancet cap", "curved portion of the lancet body", and "sloped surface of the rear end of the lancet body" have their own useful functions and effects (to be described in detail later). Accordingly, the invention can achieve the improvement of the function of the lancet, while reducing the amount of the disposal amount and manufacturing cost.

BRIEF DESCRIPTION OF THE DRAWINGS

FIG. 1 is a perspective view of a lancet according to an embodiment of the present invention, in which

FIG. 5 shows an inward flexibility of the rim portion of the lancet body.

FIG. 9 is a schematic diagram showing a difference in the attachment of the lancet body to the cylindrical lancet attachment between the prior art and the present invention.

FIG. 10 is a perspective view of a lancet according to an embodiment of the present invention, in which

FIG. 12 is a diagram for explaining a preferred embodiment of molding process (especially, a preferred embodiment at a point time during a demolding step is performed) with respect to "stepped surface 178a".

FIG. 13 is simulation results showing a reduction in weight of the lancet according to some embodiments of the present invention.

DETAILED DESCRIPTION OF THE INVENTION

The lancet of the present invention will be described in detail below with reference to the accompanying drawings.

The term "direction" as used throughout the claims and description is defined as follows: The direction in which side a lancet cap is positioned when viewed on the whole is regarded as a "forward" direction, whereas the direction in which side a lancet body is positioned when viewed on the whole is regarded as a "backward"/"rearward" direction. In other words, the "forward direction" corresponds to the direction in which a pricking component moves upon performing a pricking operation, and the reverse direction thereto is regarded as a "backward"/"rearward" direction.

Figure 1A:
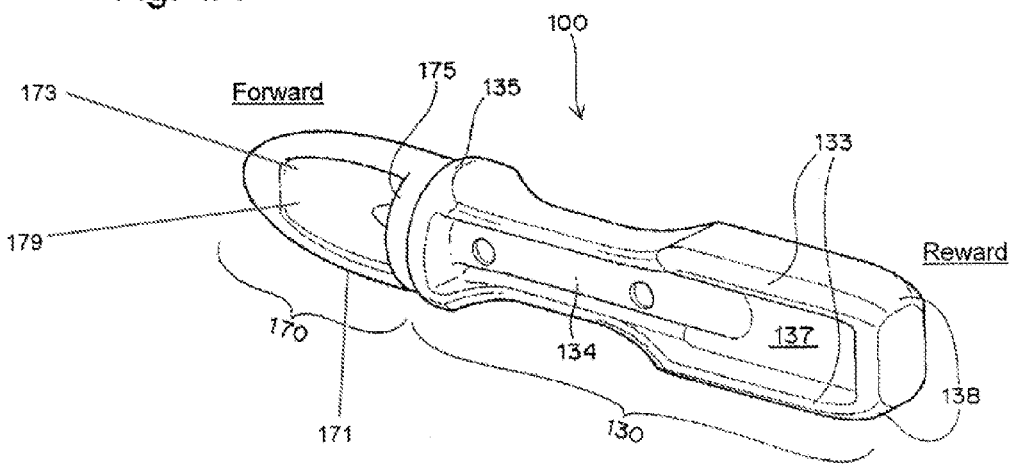
FIG. 1A shows the lancet as viewed from one side.
Figure 1B:
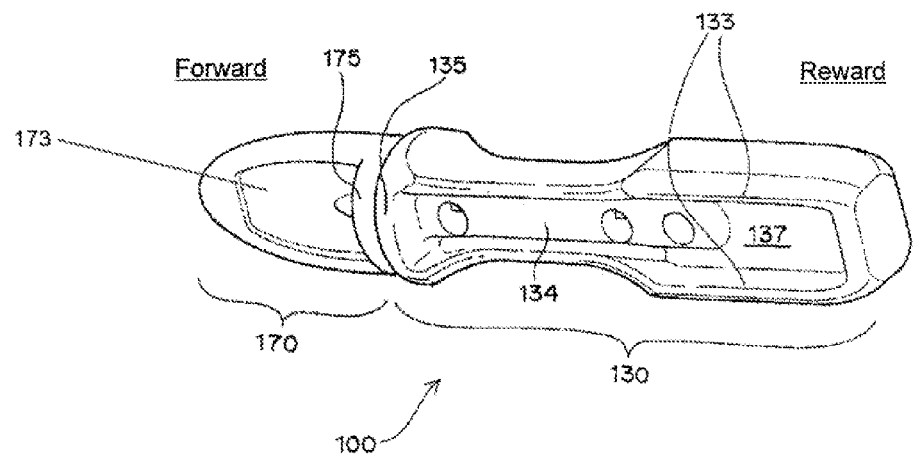
FIG. 1B shows the lancet as viewed from the opposite side to that of FIG. 1A.
Figure 2:
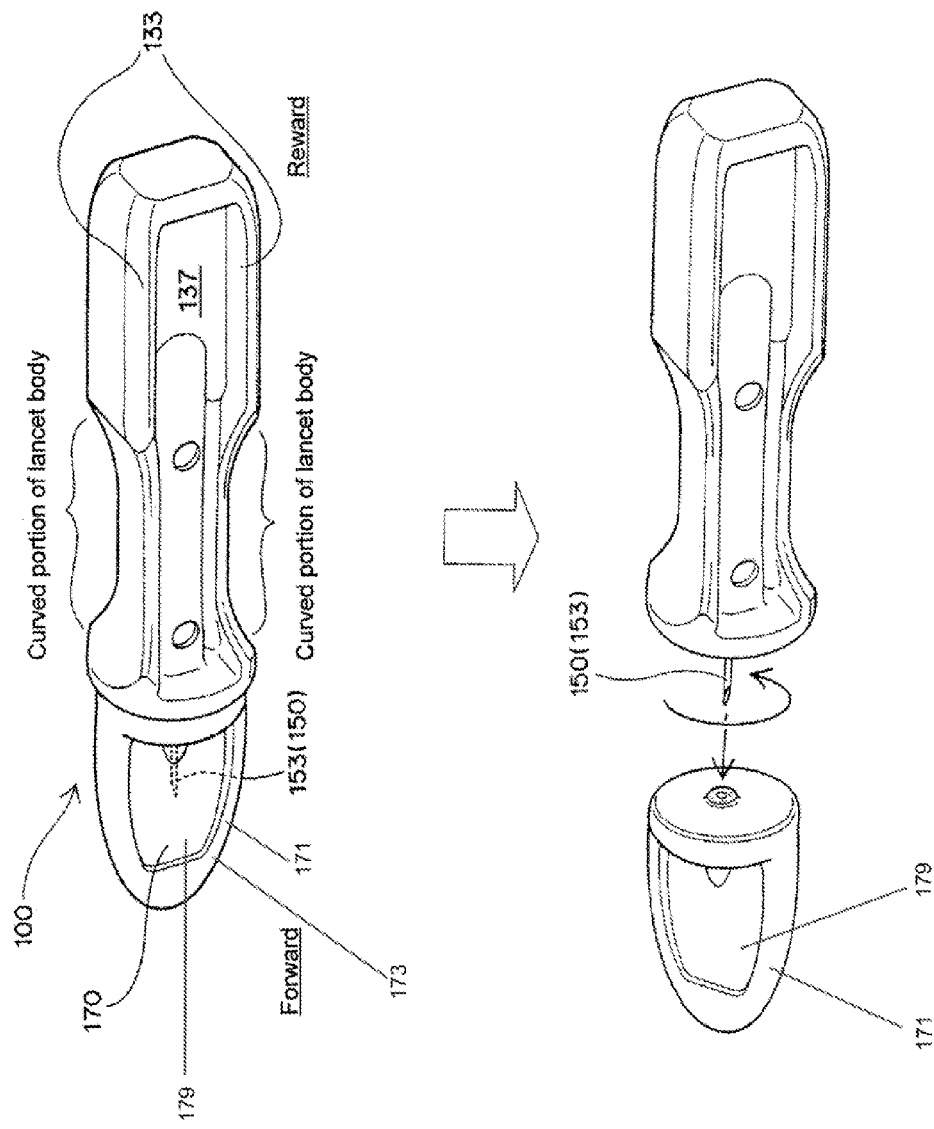
FIG. 2 is a perspective view showing the lancet with its cap removed therefrom.

FIG. 1 shows an appearance of the lancet 100 according to an embodiment of the present invention. FIG. 2 shows a developed diagram of the lancet 100 (i.e., the lancet with its cap removed). As shown in FIGS. 1 and 2, the lancet 100 of the present invention is mainly composed of a lancet body 130, a lancet cap 170 and a pricking component 150. The lancet body 130 and the lancet cap 170 are made of resin, whereas the pricking component 150 is made of metal.

The pricking component 150 can have the form of "needle" or "blade" at the tip thereof. The pricking component is situated in both of the lancet body 130 and the lancet cap 170 such that the tip 153 of the pricking component 150 is covered with the thin center portion 179 of the lancet cap 170. For this reason, the pricking component cannot be seen in FIG. 1.

The lancet cap 170 and the lancet body 130 are integrally connected to each other via only a small contact portion. The lancet 100 can be formed by inserting the pricking component 150 into a metal mold, in a so-called insert molding process. In this regard, the contact portion can be formed upon carrying out the insert molding process. Accordingly, the contact portion can be formed of the same resin as that of the lancet cap 170 and the lancet body 130. Suitable materials for the lancet body 130 and the lancet cap 170 are resin which is normally used for the lancet, such as polyethylene and polypropylene. It is, however, preferred that the materials for the lancet body and the lancet cap are a soft resin selected from the group consisting of a low density polyethylene, a high density polyethylene, a polystyrene and an elastomer. While on the other hand, the metals for the pricking component 150 are any suitable metal which is normally used for a pricking needle of a lancet in general. The metals for the pricking component may be a stainless steel, for example.

Figure 3:
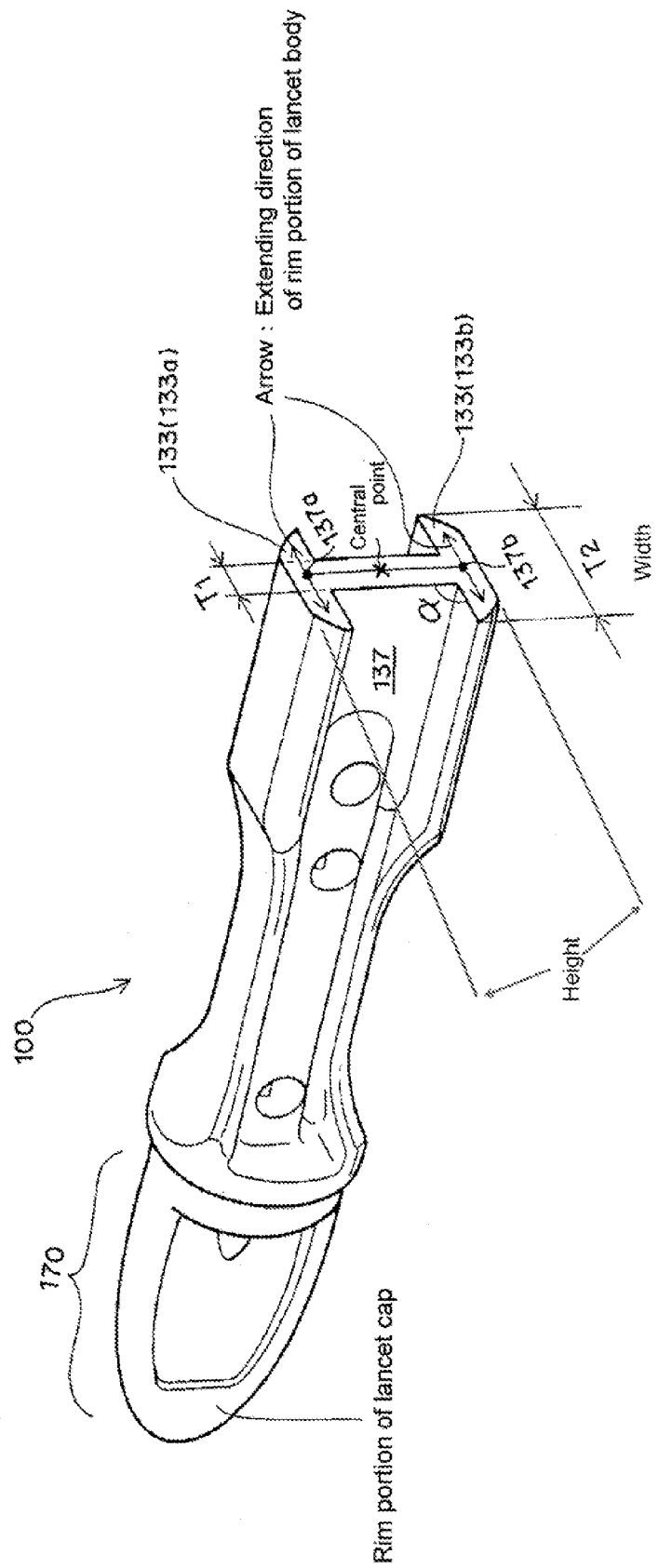
FIG. 3 is a perspective view of the lancet, showing the cross section of a lancet body of the lancet, taken along the lateral direction thereof (especially taken at the rear end side of the lancet body).

As shown in FIGS. 1, 2, and 3, the lancet body of the lancet according to the present invention is thin except its rim portion 133. In other words, most of the lancet body (especially, axis central portion extending along the pricking component and/or adjacent portion) constitutes a thinner main portion 137 of the body, whereas the rim portion 133 of the lancet body, which rim portion surrounds the thin main portion 137, constitutes a thicker portion 133 of the body.

The thickness "$T_1$" of the thinned portion 137 of the lancet body is thinner than a thickness "$T_2$" of the rim portion 133 of the lancet body, preferably by 30% to 60%, more preferably by 30% to 50%, and most preferably 40% to 50% (see FIG. 3). As clearly illustrated in FIG. 3, the "thickness" refers to the distance in the width direction of the lancet body 130. For example, the thickness (width) "$T_1$" of the thinned main portion 137 is in the range of 1.6 mm to 3.6 mm, while on the other hand the thickness (width) "$T_2$" of the rim portion 133 is in the range of 2.8 mm to 6.4 mm. By way of example, the thickness (width) "$T_2$" of the thinned portion 137 may be about 2.6 mm, while on the other hand the thickness (width) of the rim portion 133 may be about 4.6 mm. As shown in the partial cross-sectional views of FIGS. 3 and 4A, the main portion 137 extends between the two opposing sections of rim portion 133 and has a uniform width $T_1$ with flat side surfaces. As such, the lancet body is thin (i.e., has a reduced width)

except for its rim portions 133, which not only can largely reduce the weight and volume of the lancet, but also can achieve a suitable attaching/securing of the lancet to the plunger.

As shown in FIG. 3, the rim portion 133 of the lancet body extends symmetrically from the thinned main portion 137 of the lancet body. Such symmetrical rim portion 133 can more suitably serve to attach and secure the lancet to the plunger. Referring to FIG. 3, the rim portion 133 of the body extends in the direction of arrow, which shows "symmetrical extending" of the rim portion. In other words, when viewed as the transverse section of the lancet body (i.e., cross section taken along the lateral direction of the body), the rim portion 133 of the lancet body has a symmetrical form with respect to a point of the thinned portion 137. For example, sub-rim portions 133a respectively extend equally away from the edge 137a of the thinned portion 137 (see FIG. 3). Likewise, sub-rim portions 133b respectively extend equally away from the edge 137b of the thinned portion 137 (see FIG. 3). When all of the sub-rim portions 133a and 133b are considered altogether, the rim portion symmetrically extends with respect to a point of a central part of the thinned portion.

Figure 4:
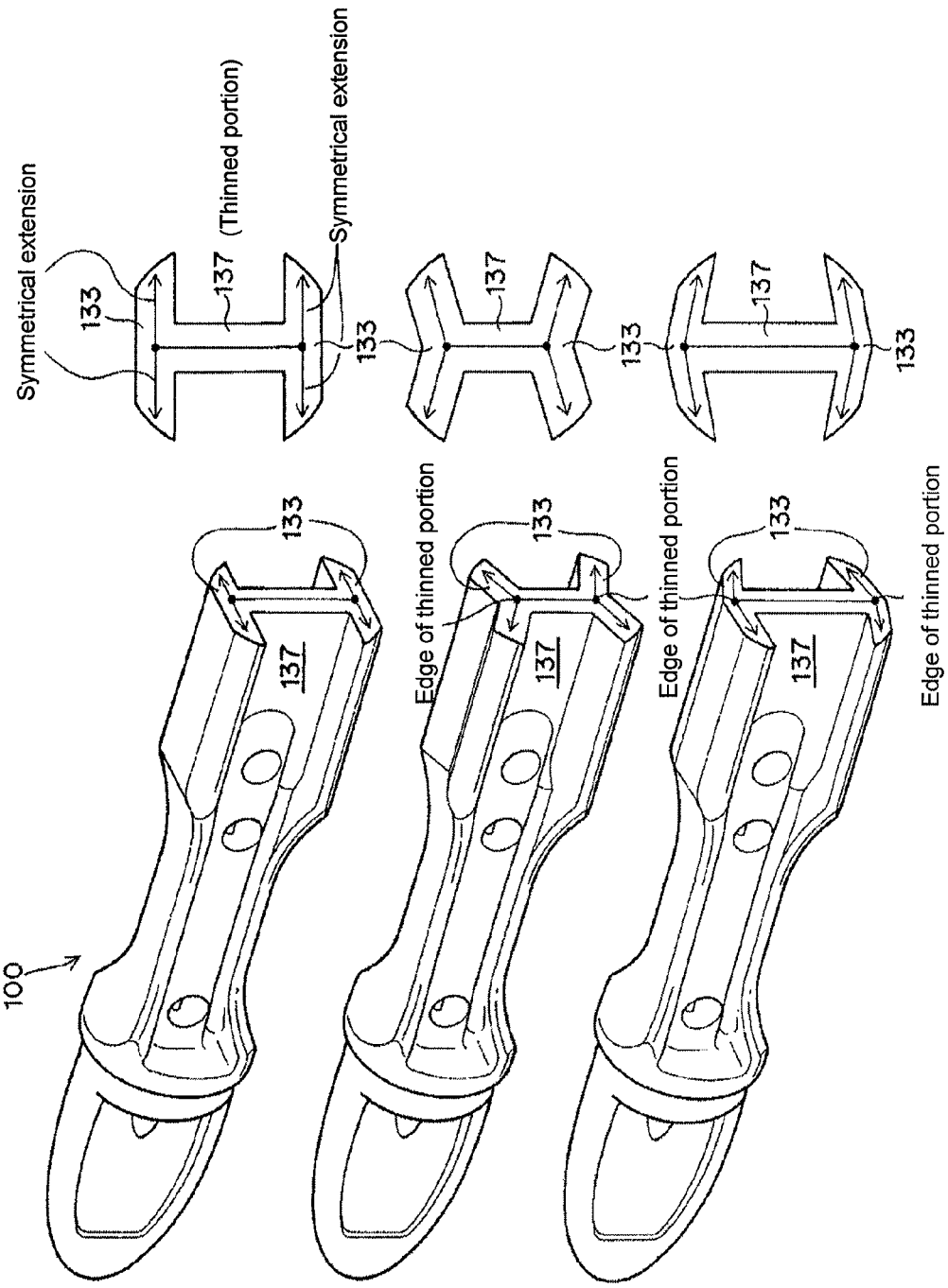
FIGS. 4A to 4C are schematic views respectively showing an embodiment of a rim portion (of the lancet body) extending symmetrically from a thinned portion of the lancet body.

With respect to the symmetrical rim portion 133, a form thereof is not limited to that shown in FIG. 3. The symmetrical rim portion 133 may have other forms shown in FIGS. 4B and 4C. That is, the symmetrical form of the rim portion 133 is not limited to that shown in FIG. 4A, but may be those shown in FIGS. 4B and 4C. Specifically, as shown in FIG. 4B, the rim portion 133 may extend from the edges of the thinned portion 137 such that the rim portion outwardly expands. While on the other hand, as shown in FIG. 4C, the rim portion 133 may also extend from the edges of the thinned portion 137 such that the rim portion inwardly expands.

According to one preferred embodiment, the rim portion 133 of the lancet body extends approximately perpendicularly with respect to the thinned portion 137 of the lancet body as shown in FIGS. 3 and 4A. That is, it is preferred that the sub-rim portions (133a, 133b) of the lancet body extend approximately perpendicularly from the edges (137a, 137b) of the thinned portion 137 of the lancet body as shown in FIG. 3. In other words, the transverse section of the lancet body (i.e., cross section taken along the lateral direction of the body) preferably has substantially "H-like shape". The phrase "approximately perpendicularly with respect to the thinned portion" as used herein substantially means an angle of 85° to 95°, preferably 87° to 93° with respect to the principal surface of the thinned portion. This means that an angle "α" shown in FIG. 3 is in the range of 85° to 95°, preferably 87° to 93°.

Figure 5:
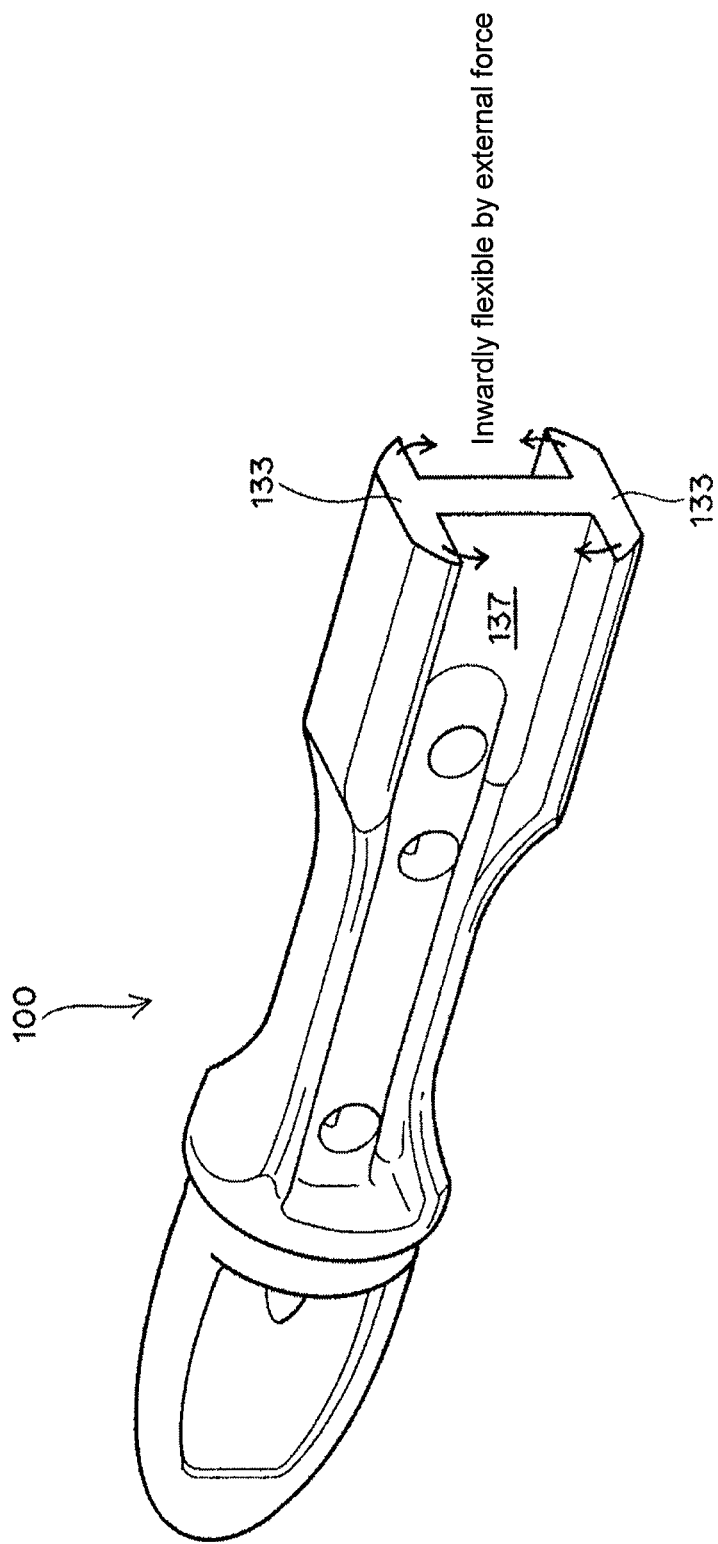
FIG. 5 is a perspective view of the lancet, showing the cross section of a lancet body, taken along the lateral direction thereof. Especially.
Figure 6:
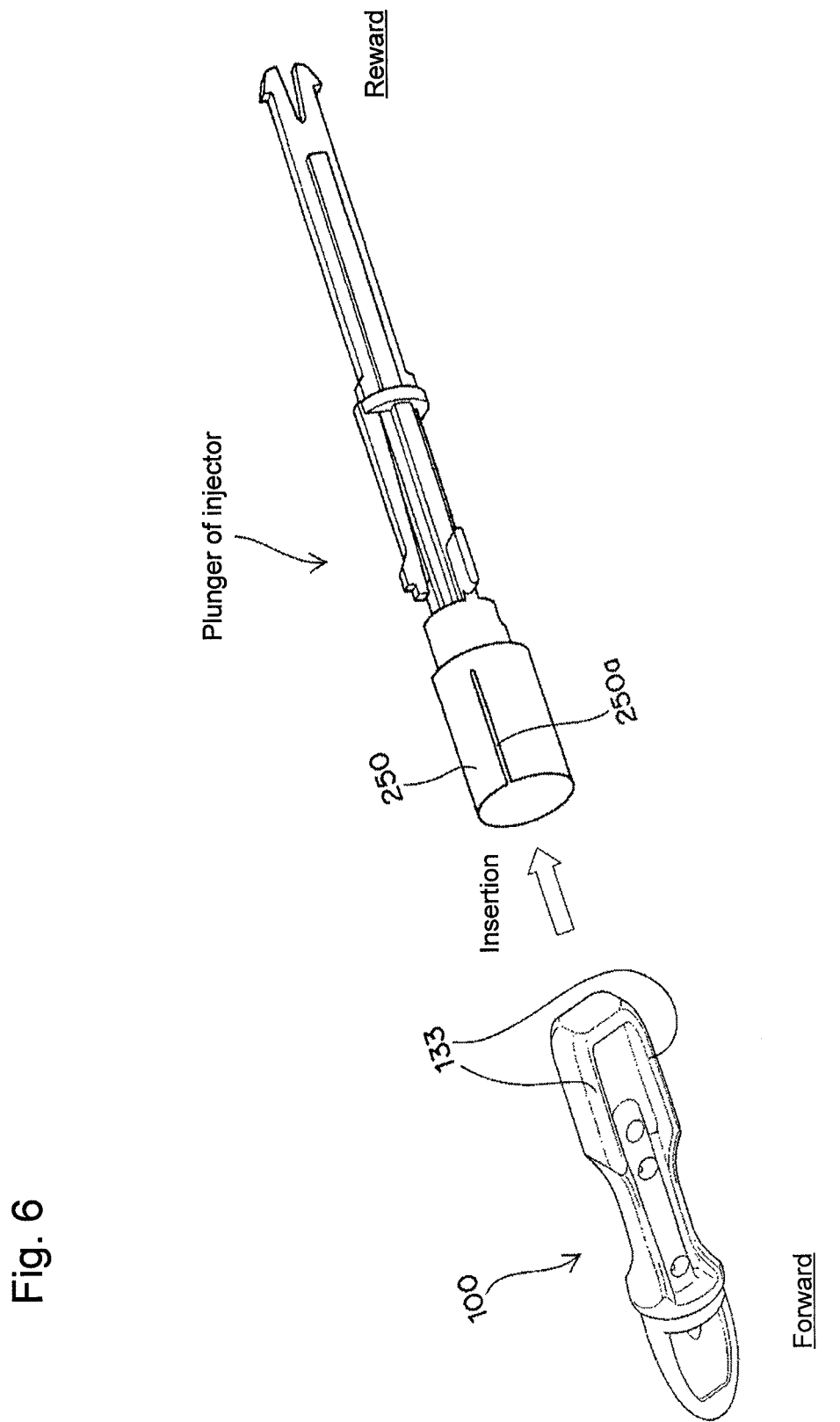
FIG. 6 is a perspective view showing an embodiment wherein the lancet is attached to a cylindrical lancet attachment provided at the tip of a plunger.

The rim portion 133 of the lancet body is suitable for the attachment of the lancet to the plunger. In this regard, it is more preferable that the rim portion 133 is flexible such that the rim portion exhibits an inward flexibility (see FIG. 5). That is, the lancet body is inwardly flexed (inwardly bent) upon being subjected to an external force. This means that, when the lancet is attached to the plunger, the rim portion of the lancet body can be inwardly flexed due to the force received from the plunger. For example, upon the attaching of the lancet to "cylindrical lancet attachment 250 provided at the tip of the plunger" (see FIG. 6), the rim portion 133 can be inwardly flexed such that the rim portion of the lancet body corresponds to the size of the cylindrical lancet attachment 250. As such, even if the cylindrical lancet attachment is designed to have somewhat smaller size, the lancet body can be flexed upon the attaching of the lancet to the plunger, and thereby the lancet is suitably fitted into the cylindrical lancet attachment. That is, even when there is a small difference in size between the cylindrical attachment and the lancet body, the lancet can be suitably fitted into the cylindrical attachment. It should be noted in this regard that the conventional cylindrical attachment of the plunger is in most cases manufactured in accordance with a variety of the existing lancets, and thus the cylindrical attachment does not have a specified size (i.e., there is no standard for size of the cylindrical attachment of the plunger), which leads to some variations in size of the cylindrical attachments.

Figure 7A:
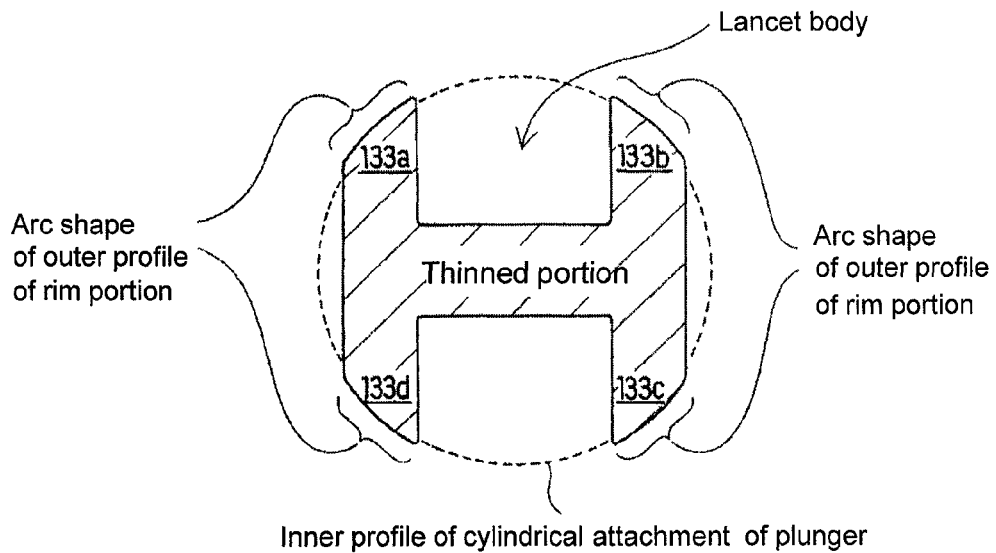
FIG. 7A is a cross-sectional view (taken along the lateral direction of a lancet body) showing an embodiment of the lancet body at a point in time before the lancet is attached to the cylindrical lancet attachment.
Figure 7B:
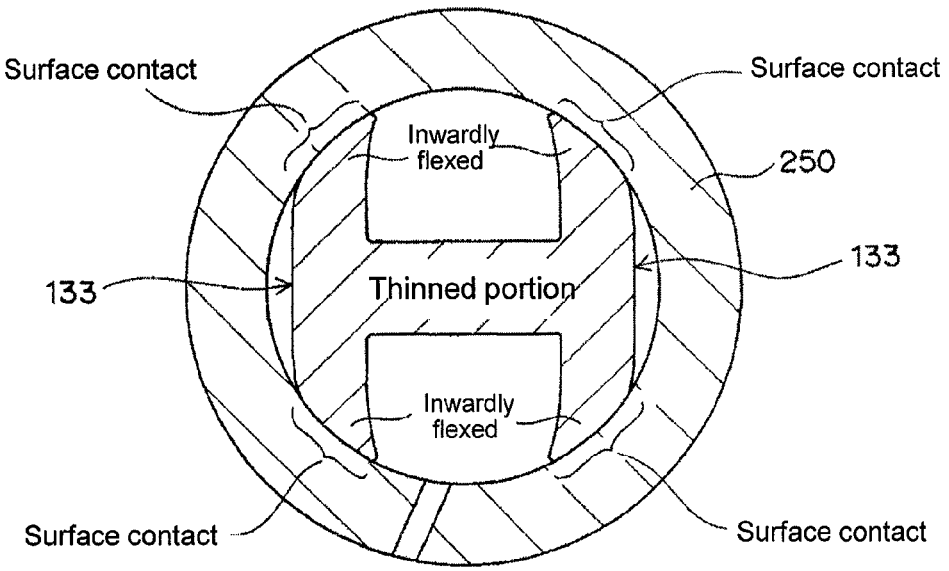
FIG. 7B is a cross-sectional view (taken along the lateral direction of a lancet body) showing an embodiment of the lancet body at a point in time after the lancet is attached to the cylindrical lancet attachment.

In accordance with the invention, the flexed rim portion 133 of the lancet body makes a contact with the cylindrical lancet attachment of the plunger, and thereby the lancet body can be attached and secured to the plunger, which leads to an achievement of the relatively strong connection of the lancet to the plunger. Particularly as shown in FIGS. 7A and 7B, the lancet body and the cylindrical attachment are not in "point contact" with each other, but in "surface contact" with each other. As shown in FIGS. 7A and 7B, the lancet body and the cylindrical attachment are in "four" surface contact with each other at four points of the rim portion, for example. As a result, the relatively strong connecting of the lancet to the plunger is achieved, which eventually allows a smooth removal of the lancet cap from the lancet.

Figure 8:
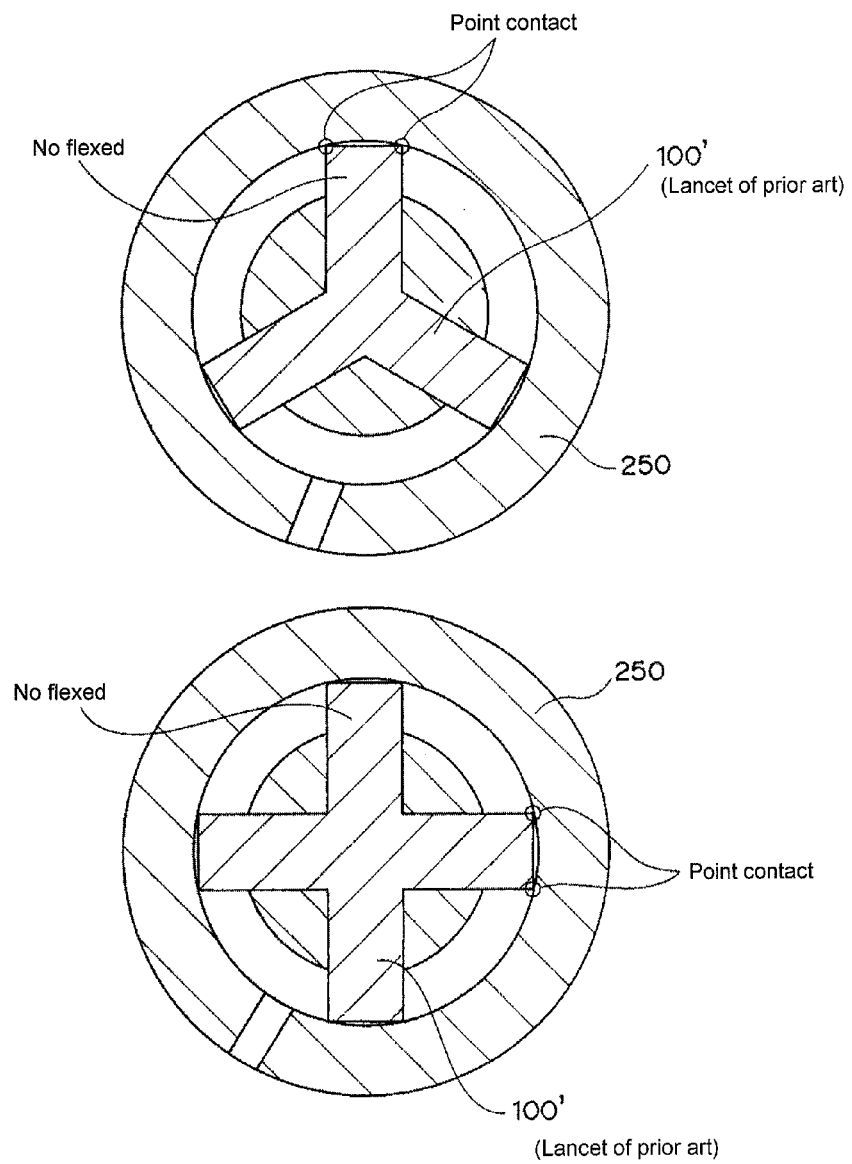
FIG. 8 is a cross-sectional view (taken along the lateral direction of a lancet body) showing an embodiment of the lancet body at a point in time after a lancet of the prior art is attached to the cylindrical lancet attachment (Prior Art).

The conventional attaching of a lancet body to a cylindrical lancet attachment in the prior art is shown in FIG. 8. As shown in FIG. 8, the lancet body itself serves as a "beam" and thus the body is not flexed in the prior art. A body of the cylindrical attachment is generally provided with a cut portion ("250a" shown in FIG. 6). In the prior art, the lancet body itself is not flexed, whereas the cylindrical attachment of the plunger is flexed to allow the fixing of the lancet body to the cylindrical attachment. That is, the attaching state as shown in FIG. 8 is brought about in the prior art, and thus the lancet body and the cylindrical attachment are in "point contact" with each other. Moreover, as shown in FIG. 9, the cylindrical attachment is expanded due to the existence of the cut portion 250a, which does not make a favorable contact between the lancet body and the cylindrical attachment. In contrast to such embodiment of the prior art, the lancet of the present invention can achieve the "surface contact" by the flexed lancet due to the existence of the rim portion 133 of the lancet body, which leads to the relatively strong contact between the lancet and the cylindrical lancet attachment.

Due to the symmetrically shaped rim portion 133, it is preferred that the rim portion 133 makes the surface contact with the cylindrical lancet attachment 250 in a form of symmetry at four points of the rim portion, as shown FIGS. 7A and 7B. As can been seen from FIG. 7B, the rim portion 133 makes the surface contact with the cylindrical lancet attachment such that the four sub-rim portions form an angle of about 90° with each other. In order to more suitably achieve the "surface contact", it is preferred that an outer profile of the rim portion of the lancet body includes an arc shape in at least a part of the rim portion (see FIG. 7A, for example). In particular, the outer profiles of the tip parts 133a to 133d of the rim portion preferably have arc shape. Due to such arc shape of the rim portion, the area of "surface contact" increases, achieving the more suitable connection between the lancet and the cylindrical lancet attachment.

In addition to the "form of the lancet body wherein the body is thin except for its rim portion 133", the form of the lancet cap can also suitably contribute to the reduction in weight and volume of the lancet. For example, the lancet cap 170 preferably has a flat (planar) shape as a whole, as shown in FIGS. 1 to 3. That is, it is preferred that the entire form of a main portion 173 of the lancet cap 170 is flat (planar). The flat-shaped main portion 173 of the lancet cap having a rim portion 171 and a center portion 179 not only contributes to the reduction in weight and volume of the lancet as a whole, but also contributes to an improved function of the lancet because the cap can be easily held with the finger of the user. Upon removal of the cap from the lancet, the lancet cap 170 is to be "wrenched"/"twisted off". The lancet cap 170 may have the suitable form for this removal operation. Specifically, it is preferred that the main portion 173 of the flat cap 170 has the thin center portion 179 which is thinner than the rim portion 171 of the cap (i.e., the center portion 179 has a smaller thickness in a width direction of the planar main portion 173 than the rim portion 171). In this case, the finger of the user cannot be slipped off the cap during the removal operation of the lancet cap, such removal operation of the lancet cap from the lancet body being performed by twisting the cap around its central axis (see FIG. 3). More specifically, the ball of the finger is suitably held in a boundary area between the rim portion of the cap and the thinned portion thereof upon removing the cap, which brings about a desired holding power in the lancet cap during the removal thereof.

It is preferred in the lancet of the present invention that a front end of the lancet body 130 is provided with a flange portion "A" 135 (see FIG. 1). That is, the lancet body 130 is preferably formed such that it has the flange portion at its front end. The flange portion "A" 135 of the lancet body can serve as a holding part during the attaching/securing of the lancet to the plunger. Specifically, the presence of the flange portion "A" 135 allows the lancet body to be smoothly attached to the cylindrical attachment of the plunger by holding the lancet body with the finger, not holding the "lancet cap in which the tip of the pricking component is included" with the finger, which leads to an avoidance of the inconveniences (e.g., "adverse bending" of the pricking component). Moreover, the flange portion "A" works well at a point in time after the pricking operation. Specifically, the flange portion "A" 135 can be suitably held with the finger so as to pull out the lancet upon the removal of the lancet from the cylindrical lancet attachment of the plunger.

Similarly to the body flange portion "A" 135 of the lancet body 130, it is preferred that a rear end of the lancet cap 170 is provided with a cap flange portion "B" 175 (see FIG. 1). That is, the lancet cap 170 is preferably formed such that it has the cap flange portion at its rear end. As shown in FIG. 1, it is preferred that the cap flange portion "B" 175 of the lancet cap 170 is opposed to the flange portion "A" 135 of the lancet body and that both flange portions are symmetrical with respect to a longitudinal axis of the pricking component 150. As such, the body flange portion "B" 175 can be held together with the flange portion "A" 135 by the user during the attaching and securing of the lancet to the plunger, which leads to a stable attaching operation. In this regard, it should be noted that an insertion depth of the lancet with respect to the cylindrical attachment may vary depending on the type of the injector. Thus, the integral holding of the cap flange portion "A" 135 and the body flange portion "B" 175, i.e., the integral holding of the forward-side portion of the lancet can bring about an increase in flexibility of the insertion/attachment operation. Moreover, the existence of the flange portion "A" 135 and the flange portion "B" 175 means that lancet's portions around such flange portions are relatively thin, which also contributes to a reduction in the weight and volume of the lancet.

In order to more suitably perform the insertion/attaching of the lancet into the cylindrical attachment of the plunger, a rear end of the lancet body 130 may have a sloped surface 138 (see FIG. 1). That is, it is preferred that the width of the rear end portion of the lancet body (i.e., body dimension along the lateral direction of the lancet at the rear end portion of the lancet body) gradually decreases toward the reward direction of the lancet. The sloped surface itself may be in a form of a plane surface or a curved surface. The existence of the "sloped surface 138" means that the lancet has a partly removed end portion therein, which also contributes to a reduction in the weight and volume of the lancet.

Additionally, in order to more suitably perform the inserting/attaching of the lancet into the cylindrical attachment or detaching of the lancet therefrom, the form of the lancet body may be suitably modified. For example, the lancet body may have a curved portion such that a width of the lancet body (i.e., body dimension along the lateral direction of the body) gradually decreases (see FIG. 2). As shown in FIG. 2, the lancet body may have a "concave R-shape" at its lateral side, which allows the lancet to be more suitably detached from the cylindrical attachment. The existence of the "curved portion/concave R-shaped part" means that the lancet body has a partly narrowed portion therein, which also contributes to a reduction in the weight and volume of the lancet.

Figure 22:
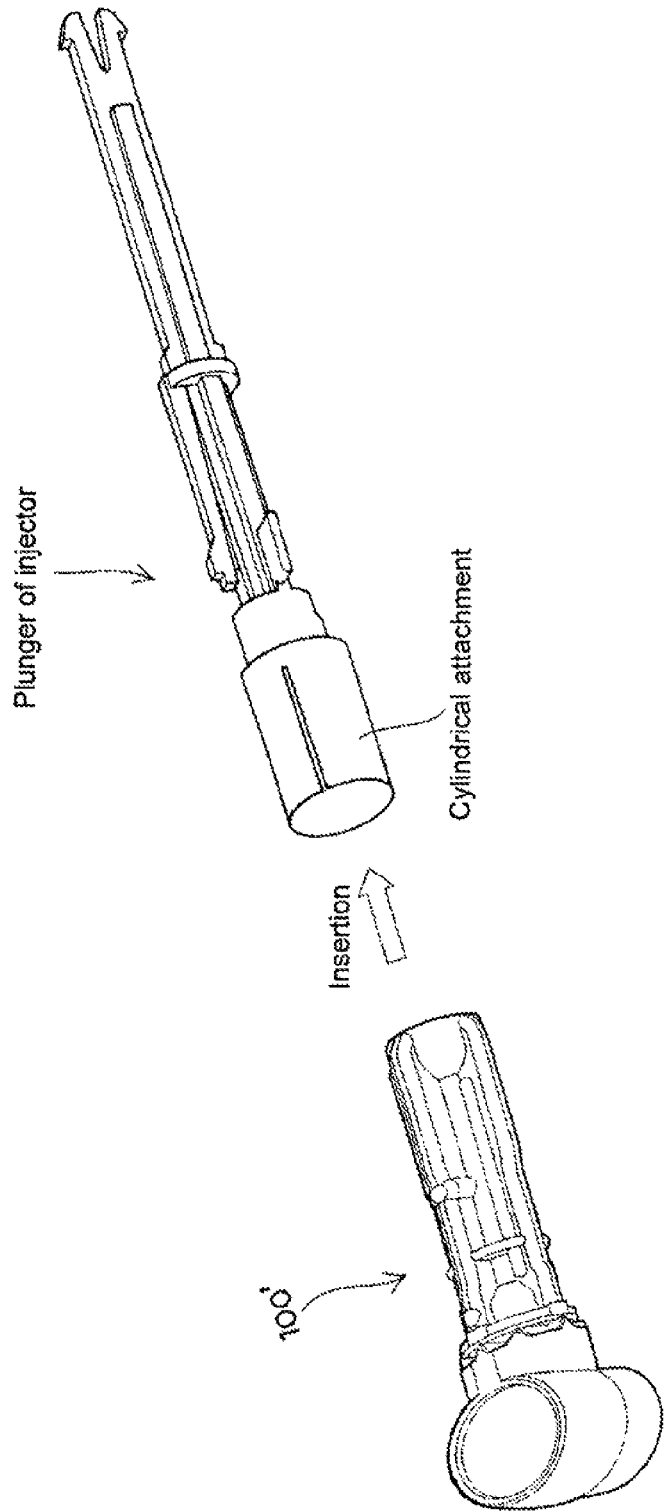
FIG. 22 is a perspective view showing an embodiment wherein the lancet of the prior art is attached to a cylindrical lancet attachment provided at the tip of a plunger (Prior Art).

In the lancet of the invention described above, the combination of "thinned portion of the lancet body", "flat-shaped lancet cap", "flange portion "A" of the lancet body/flange portion "B" of the lancet cap", "sloped surface of the rear end of the lancet body", "curved portion of the lancet body" and so on serve to reduce the reduction in weight and volume of the lancet by about 50% to about 65% (for example, 55% to 65%) as compared to the conventional lancet (e.g., the prior art lancet 100' shown in FIG. 13 or 22). In particular, the invention can achieve the improved function of the lancet while reducing the weight and volume of the lancet. If the volume of the lancet material is decreased so as to reduce the cost without any measures, some inconveniences may be usually brought about. Specifically, the securing of the needle might be made unstable, and the function of the lancet might also become impaired partially. The present invention overcomes such inconveniences, and thus both the "reduction in weight and volume" and the "improvement of the function" are realized. The lancet of the present invention has the form (design) to more effectively reduce a variation in thickness so as to suppress the "deformation due to the molding", as compared to the conventional lancet 100'. Further, the lancet of the present invention has a concept that a bearing surface (which is indicated by reference numeral "134" in FIG. 1) has a flat surface, and thus the lancet has such a form (form design) that it can prevent the so-called "thin burr" from occurring therein.

Figure 10A:
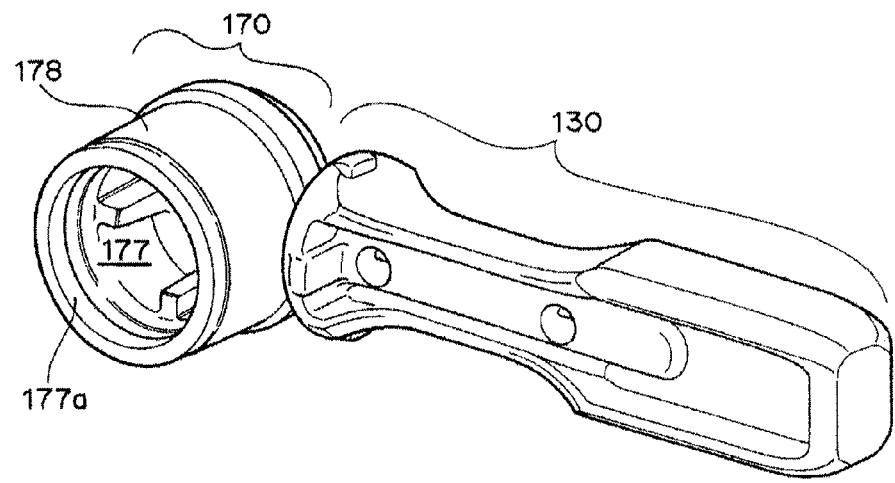
FIG. 10A shows the lancet as viewed from one side.
Figure 10B:
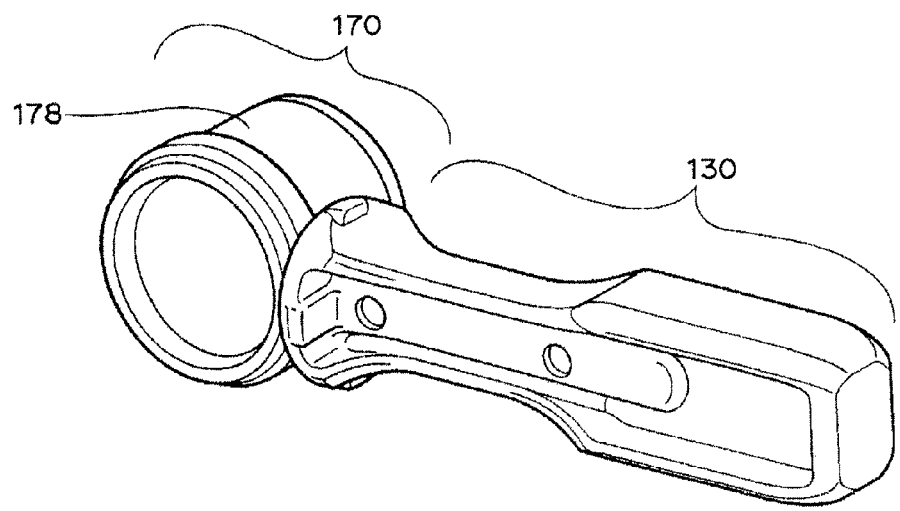
FIG. 10B shows the lancet as viewed from the opposite side to that of FIG. 10A.
Figure 11:
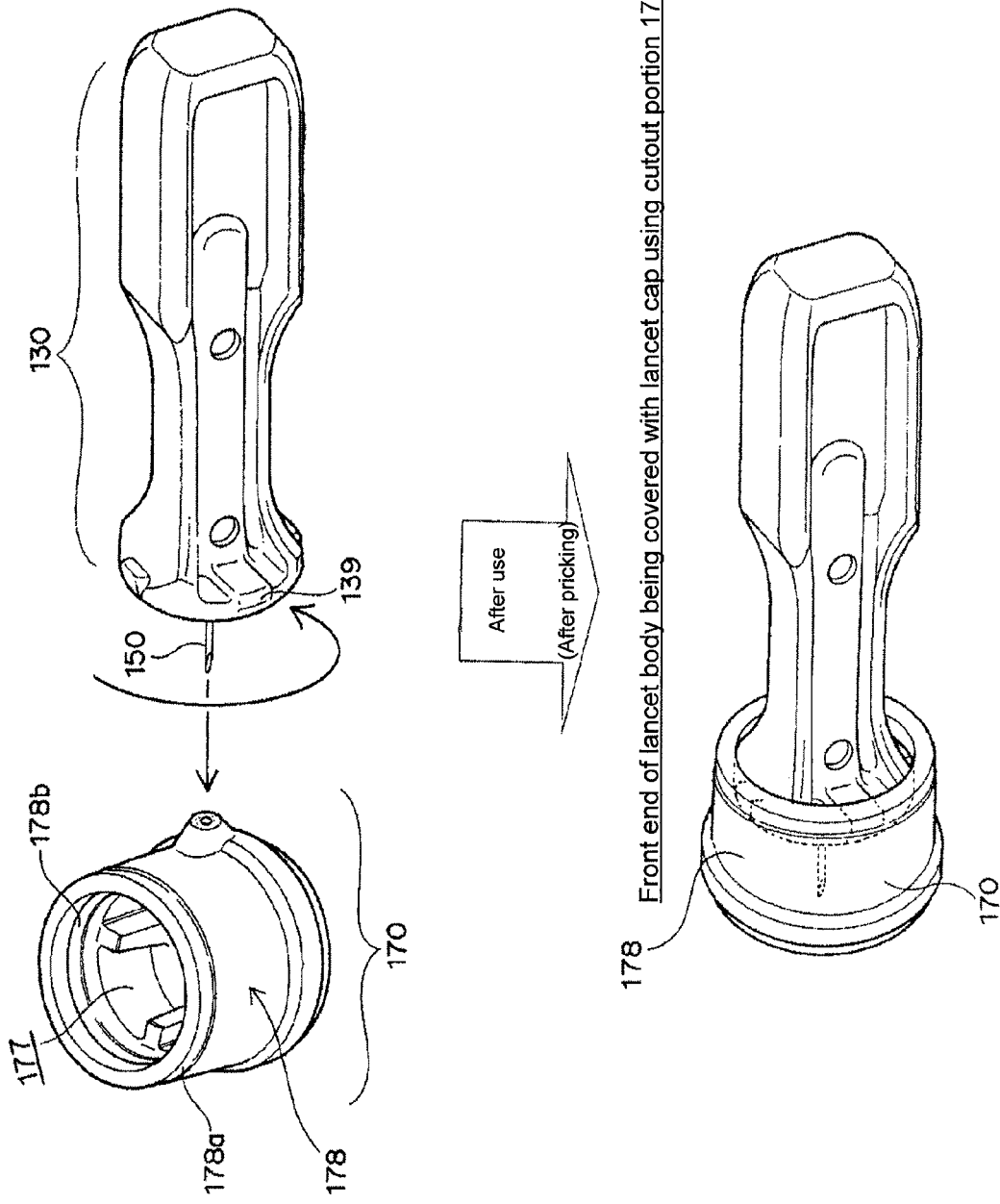
FIG. 11 is a perspective view showing an embodiment wherein a cap of the lancet of FIG. 10 is removed from the lancet, and also showing an embodiment where the pricking component of the lancet is covered with the cap at a point in time after the lancet is used.
Figure 14:
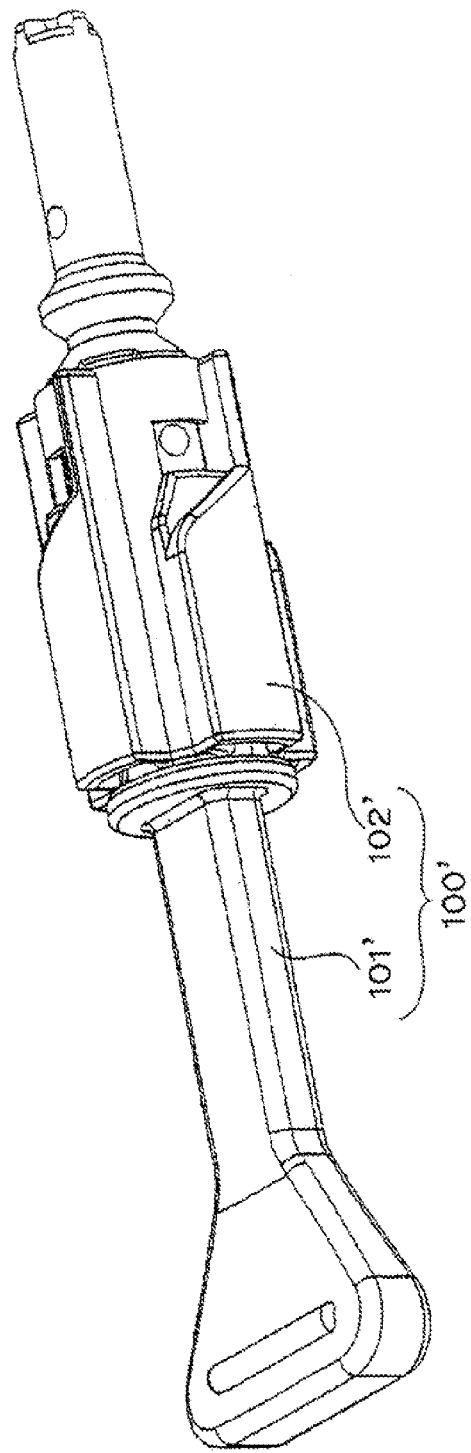
FIG. 14 is a perspective view showing an appearance of a lancet (Prior Art).
Figure 15:
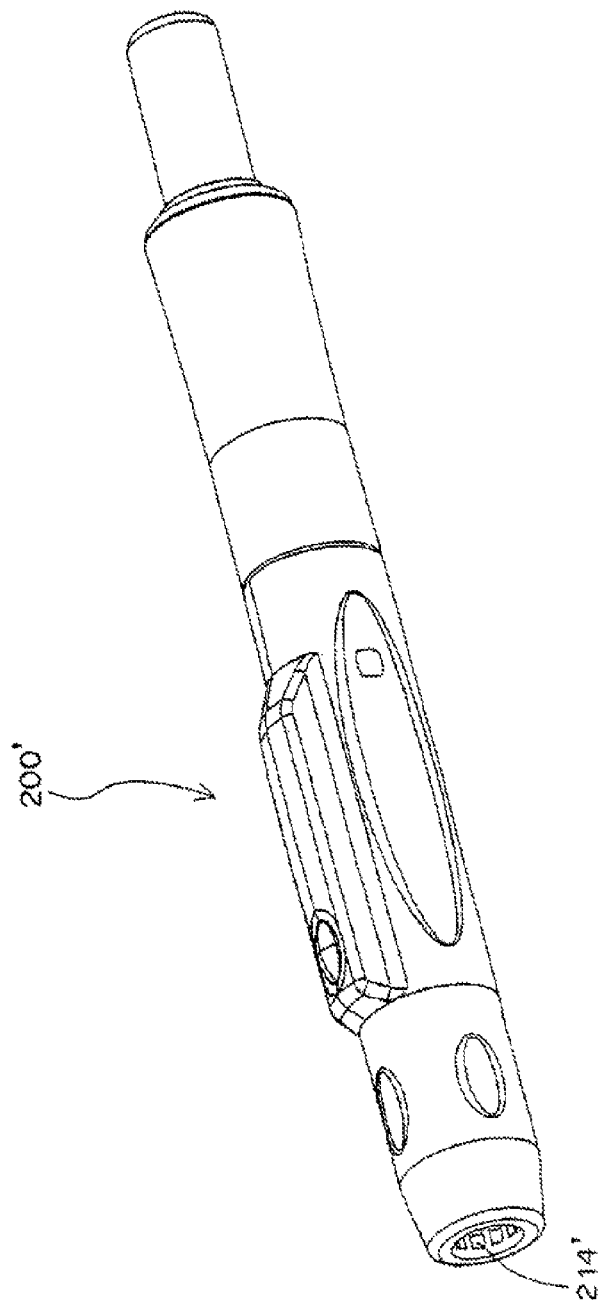
FIG. 15 is a perspective view showing an appearance of an injector (Prior Art).
Figure 16:
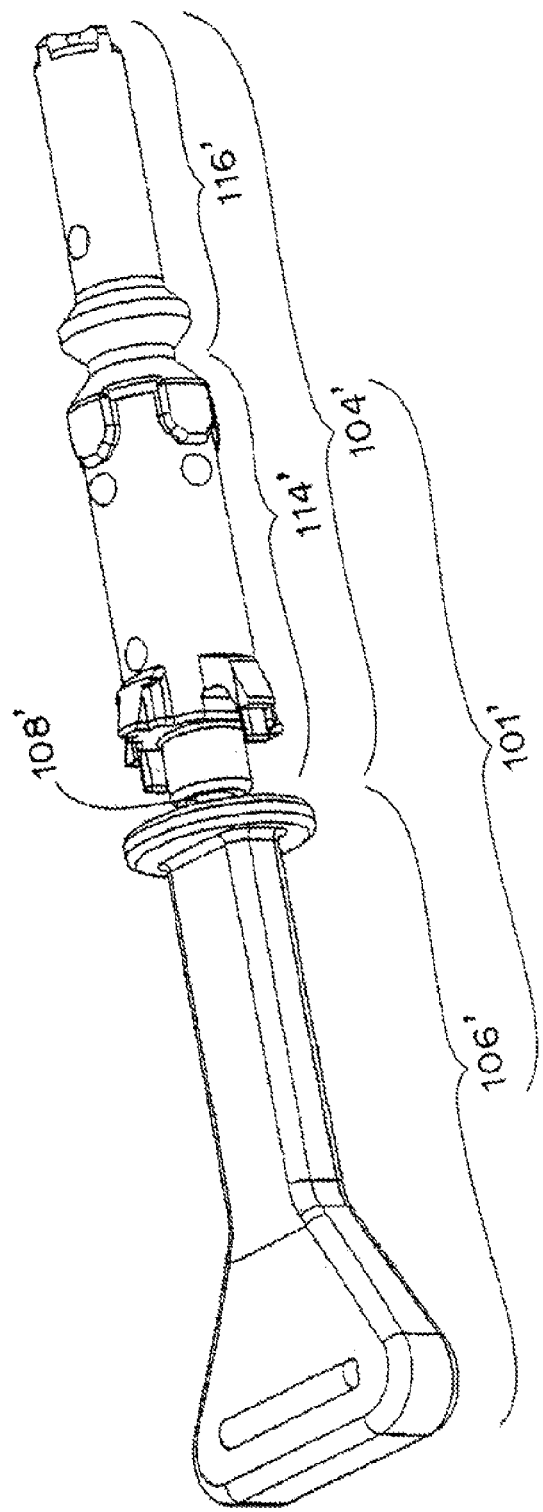
FIG. 16 is a perspective view showing an appearance of a lancet (Prior Art).
Figure 17:
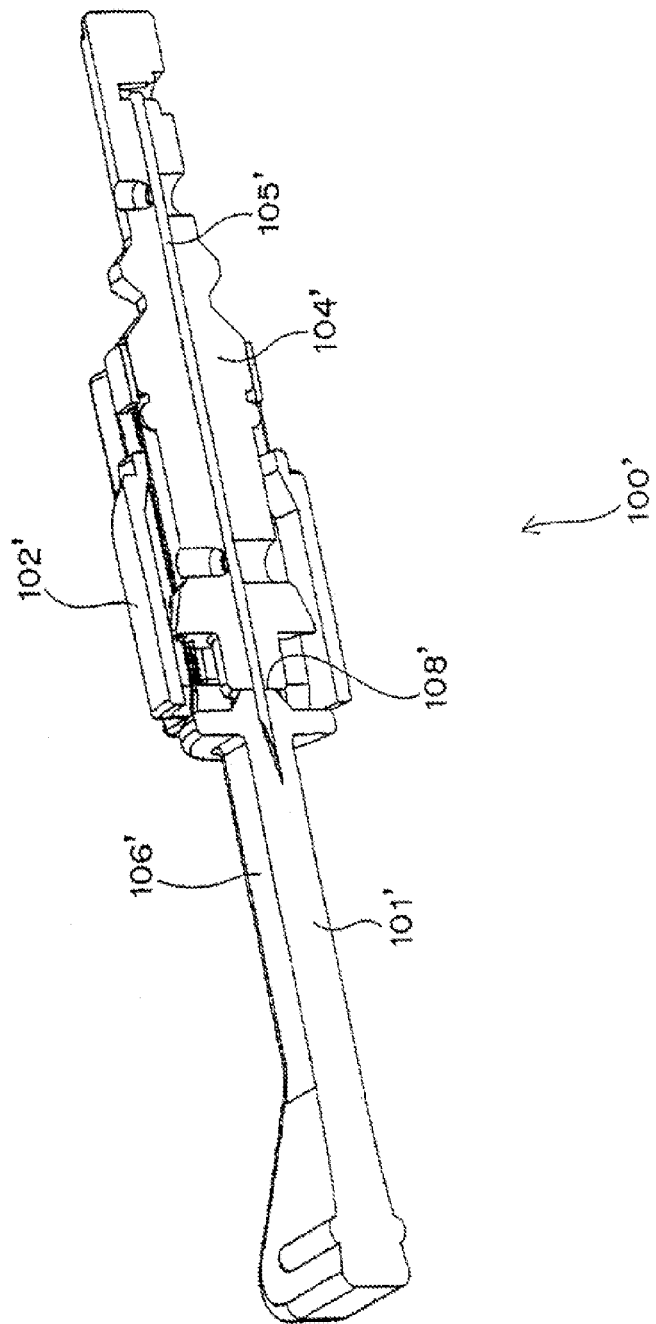
FIG. 17 is a perspective view showing a lancet of FIG. 14, cut away in half so as to make it easy to understand the inside of the lancet (Prior Art).
Figure 18:
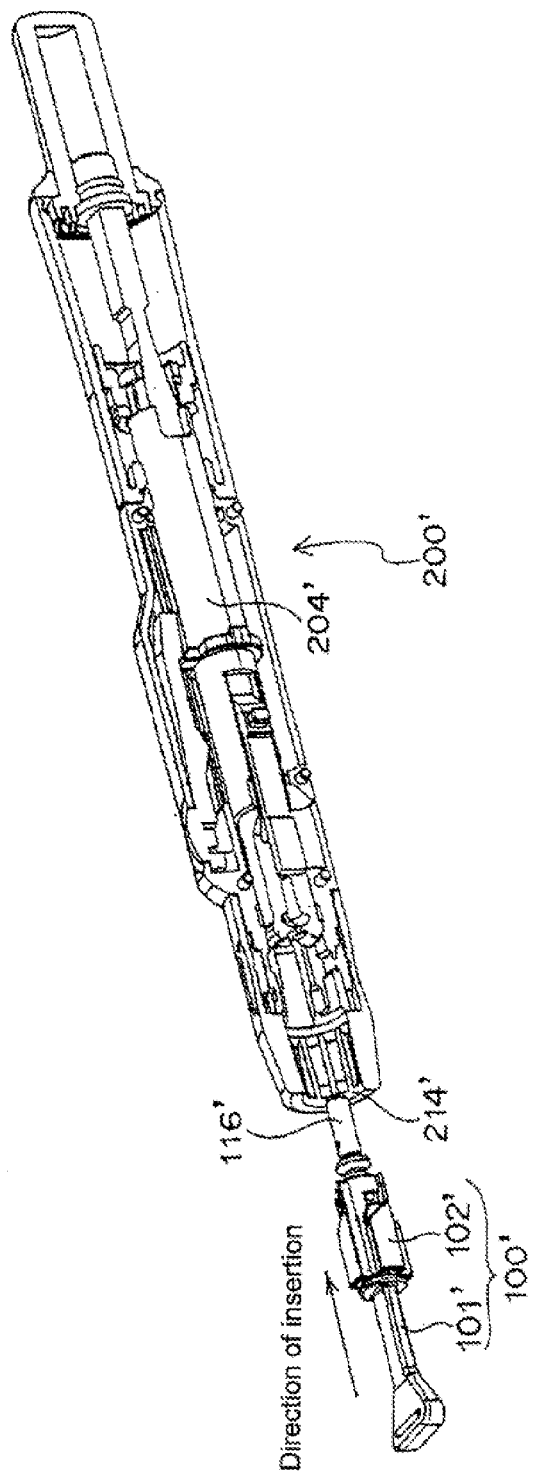
FIG. 18 is a perspective view showing the state before a lancet is loaded into an injector (Prior Art).
Figure 19:
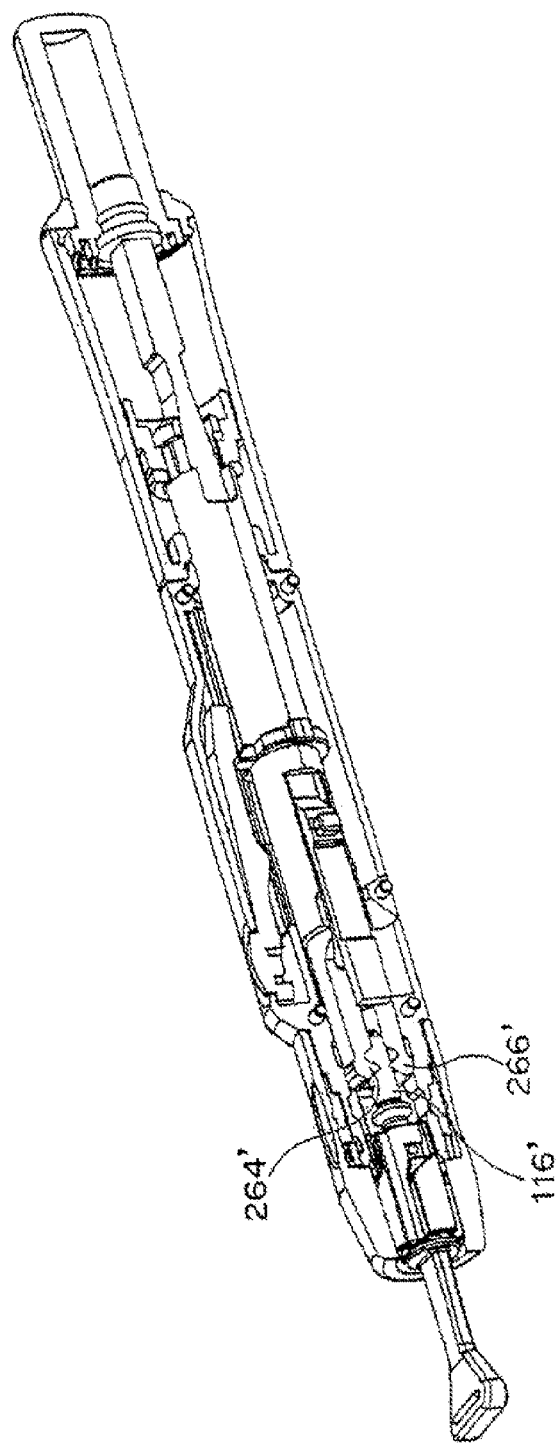
FIG. 19 is a perspective view showing the state in which a lancet is held by the tip of a plunger upon loading a lancet (Prior Art).
Figure 20:
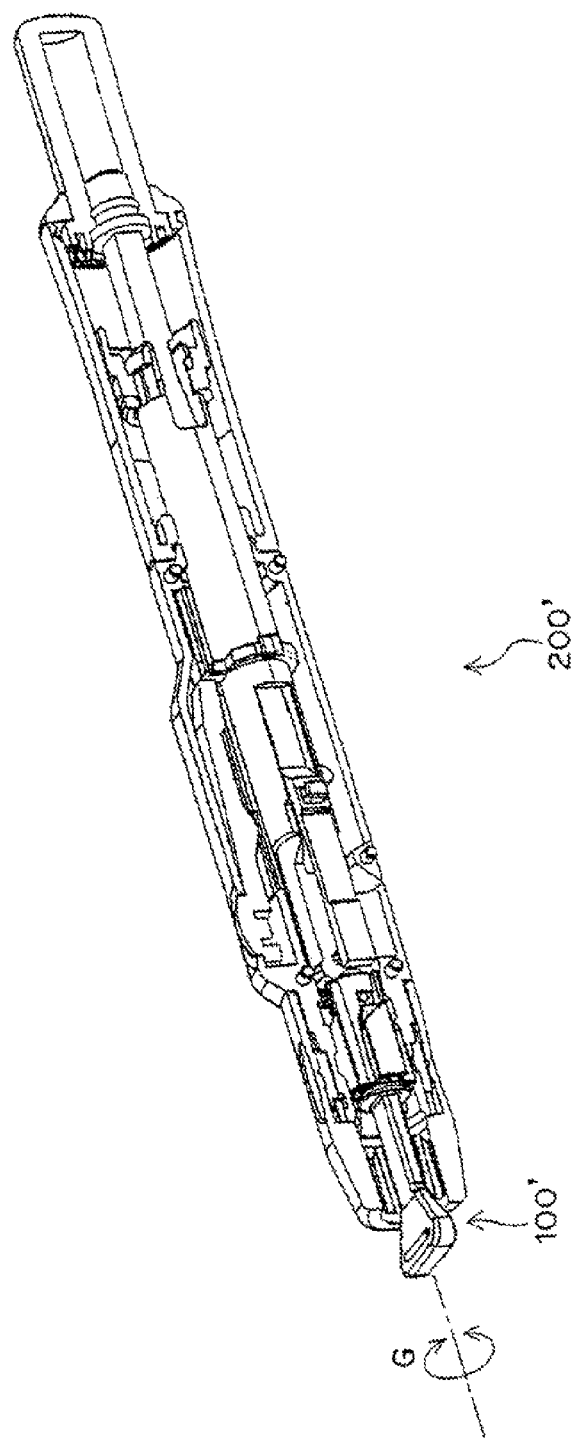
FIG. 20 is a perspective view showing the state of completion of loading a lancet wherein a plunger cannot be retracted any more (Prior Art).
Figure 21:
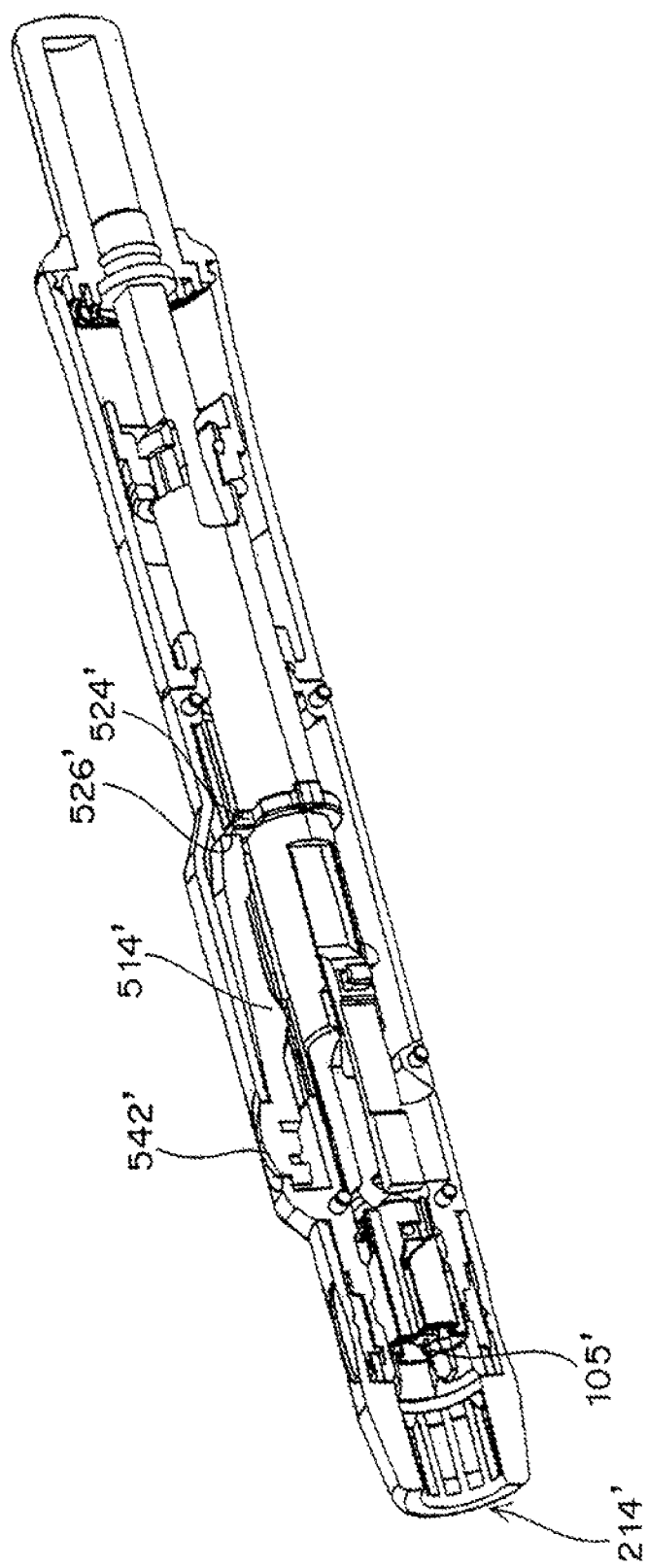
FIG. 21 is a perspective view sowing the state in which a lancet cap has been removed and thus a lancet is ready for pricking (Prior Art).

The lancet of the present invention may have an alternative form shown in FIGS. 10A and 10B other than that of FIGS. 1 to 3. In the form shown in FIGS. 10A and 10B, a cutout portion 177 is provided in the lancet cap 170. That is, the lancet cap 170 may have the hollow portion 177 with its opening mouth 177a provided at the lateral side of the cap, as shown in FIG. 10. The cutout portion 177 can be used to shield the pricking component 150 from the outside after the use of the lancet, as shown in FIG. 11. Specifically, at a point in time after the lancet is used, the lancet cap 170 can be put over the tip of the pricking component such that the cutout portion 177 is positioned around the tip part of the pricking component 150. Thus, the lancet can be disposed of without touching the used pricking component, which can improve the hygiene and safety of the lancet.

According to the above lancet of the invention, a periphery portion 178 of the cap, which portion defines the cutout portion 177 (especially defines an opening mouth of the cutout portion), has a stepped outer surface 178a (see FIG. 11). Such stepped surface 178a can mainly contributes to not only the optimization of molding process, but also the reduction in weight and volume of the lancet. As for the optimization of the molding process, the "stepped surface 178a" itself brings no extra thick part of the lancet so that such negative-angle part can be smoothly demolded (smoothly mold-released) from the metal mold. This can prevent the adverse compression and deformation of the molded lancet upon the demolding from the metal mold. Actually, the prior art can cause an undesirable demoloding process. Specifically, as shown in FIG. 12, upon ejecting/demolding the molded cap from the metal mold, the portion "A" might be compressed, and thereby causing "burr" in the molded cap. In contrast, in the invention, the outer surface has been partially removed in advance (that is, the stepped portion 178a is provided at the outer surface of the cap), which allows the portion "A" to be flexed upon the demolding of the cap from the metal mold. As a result, the present invention can avoid an adverse "defect/plucked phenomenon" attributed to the demolding of the metal mold.

Moreover, the existence of the stepped surface of the cap means that the cap has a partly removed part at its outer side. As a result, the cap's periphery portion 178 defining the cutout portion 177 can be relatively uniformly cooled for a short time during the molding process, which leads to a highly accurate shape of the cap. That is, the cap's peripheral portion 178, which is in an entirely thin form according to the present invention, makes it possible to reduce an undesirable difference in time of material solidification among local positions of the cap. This can facilitate the demoloding operation wherein the molded cap is demolded from the metal mold, such demoloding operation being usually performed after the sufficient solidification of the entire cap material.

When the tip of the pricking component is shield by disposing the lancet cap 170 over the tip of the pricking component at a point in time after the use of the lancet, a protrusion 139 of the lancet body is fitted into an inner surface groove 178b of the cap's peripheral portion 178 (see FIG. 11). The stepped surface 178a itself of the cap provides an appropriate holding force for such fitting. Specifically, the thin edge of the cap's peripheral portion, which thin edge is attributed to the presence of the stepped surface 178a, makes it possible to perform the suitable fitting of the lancet cap 170 with an appropriate force, not with an excessive force.

The existence of the "stepped surface 178b" means that the cap's peripheral portion 178 has a partially removed part at it outer side, which also contributes to a reduction in the weight and volume of the lancet.

Although some embodiments of the present invention have been hereinbefore described, such embodiments are only for illustrative purpose as typical examples, and thus the present invention is not limited to these embodiments. It will be readily appreciated by those skilled in the art that various modifications are possible without departing from the scope of the invention. For example, the pricking component 150 has a "needle form" whose uppermost is wholly sharpened in the accompanying drawings, but is not necessarily limited thereto. The pricking component 150 may have a "blade form" with only one side face of its tip sharpened, for example.

EXAMPLES

The "reduction in weight" of the lancet according to the present invention was confirmed using simulation by comparing to that of the lancet of the prior art.

FIG. 13 shows a table of the results for the simulation. As can be seen from the table of FIG. 13, the lancet according to an embodiment of the present invention (i.e., cutout cap-type lancet) had 60.0 weight percent of that of the prior art lancet, and also another lancet according to another embodiment of the present invention (i.e., flat head-type lancet) had 42.4 weight percent of that of the prior art lancet, respectively. Especially as for the flat head-type lancet, it has found that the lancet of the present invention can reduce its weight by 50% or more, and preferably by about 50% to about 65% as compared to the prior art lancet.

INDUSTRIAL APPLICABILITY

The lancet of the present invention can be used for taking the blood sample of diabetic, but the use of lancet is not limited to that. The lancet of the present invention can also be used in various applications requiring blood samples.

CROSS REFERENCE TO RELATED PATENT APPLICATION

The present application claims the right of priority of Japanese Patent Application No. 2012-25246 (filed on Feb. 8, 2012, the title of the invention: "LANCET"), the disclosures of which are all incorporated herein by reference.

REFERENCE NUMERALS

100 Lancet
130 Lancet body
150 Pricking member
153 Tip of pricking component
133 Rim portion of lancet body
133a-133d Tip part of rim portion of lancet body
134 Bearing surface
135 Flange portion "A" provided at front end of lancet body
137 Thinned portion of lancet body (web of lancet body)
137a, 137b Edge of thinned portion of lancet body
138 Sloped surface
139 Body's protrusion to be fitted into inner surface groove of cap periphery
170 Lancet cap
175 Flange portion "B" provided at rear end of lancet cap
177 Cutout portion of lancet cap
177a Opening mouth surface of cutout portion
178 Cap periphery defining cutout portion
178a Stepped surface provided in cap periphery defining cutout portion
178b Inner surface groove of cap periphery to be fitted to body's protrusion.
250 Cylindrical lancet attachment provided at the tip of plunger
100' Lancet (Prior Art)
101' Lancet
102' Protective cover
104' Lancet body
105' Pricking component
106' Lancet cap
108' Weakened part
114' Front portion of Lancet assembly
116' Rear portion of Lancet assembly
200' Injector
204' Plunger
214' Front end opening of injector
264', 266' Tip of plunger
514' Trigger component
524' Projection of plunger
526' Rear edge of trigger component
542' Press part of trigger component

The invention claimed is:

1. A lancet comprising:
   a lancet body made of resin;
   a lancet cap made of resin; and
   a pricking component made of metal, said pricking component being arranged in said lancet body and said lancet cap such that a tip of said pricking component is covered by said lancet cap;
   wherein said lancet body extends along said pricking component in a longitudinal direction of said pricking component, said lancet body having a main portion surrounding said pricking component and a rim portion surrounding said main portion, said lancet body being configured such that said main portion has a flat side surface extending between sections of said rim portion located at opposite ends of said main portion;
   wherein said rim portion is symmetrical with respect to a central point of said main portion in a cross-section through said lancet body perpendicular to said longitudinal direction of said pricking component;
   wherein said rim portion of said lancet body is flexible such that said rim portion exhibits an inward flexibility;
   wherein at least a longitudinal section of an outer profile of said rim portion of said lancet body is concave in both a direction toward said main portion of said lancet body along a height of said lancet body and a direction along a width of said lancet body; and
   wherein a width of said main portion of said lancet body is smaller than a width of said rim portion of said lancet body by an amount in a range of 30% to 60%.

2. The lancet according to claim 1, wherein said rim portion of said lancet body extends outwardly in a direction perpendicular with respect to said main portion of said lancet body.

3. The lancet according to claim 1, wherein a rear end of said lancet body has a sloped surface.

4. The lancet according to claim 1, wherein a cross-section of said lancet body has an approximately H-shaped configuration.

* * * * *